United States Patent [19]
Eichler et al.

[11] Patent Number: 4,829,986
[45] Date of Patent: May 16, 1989

[54] LITHOTRIPSY WORK STATION

[75] Inventors: Juergen Eichler, Nuremberg; Franz Grasser, Eggolsheim; Sylvester Oppelt, Bamberg, all of Fed. Rep. of Germany

[73] Assignee: Siemens Aktiengesellschaft, Berlin and Munich, Fed. Rep. of Germany

[21] Appl. No.: 72,764

[22] Filed: Jul. 13, 1987

[30] Foreign Application Priority Data

Aug. 22, 1986 [DE] Fed. Rep. of Germany ....... 3628502

[51] Int. Cl.⁴ ............................................. A61B 17/22
[52] U.S. Cl. .................................. 128/24 A; 128/328; 378/181; 378/205
[58] Field of Search ............. 128/653, 660, 659, 24 A, 128/328; 378/20, 99, 205, 181, 177, 195

[56] References Cited

U.S. PATENT DOCUMENTS

| | | | |
|---|---|---|---|
| 4,259,725 | 3/1981 | Andrews et al. | 378/901 |
| 4,543,959 | 10/1985 | Sepponen | 128/653 |
| 4,559,641 | 12/1985 | Caugant et al. | 378/205 X |
| 4,609,940 | 9/1986 | Born et al. | 378/205 X |
| 4,620,545 | 11/1986 | Shene et al. | 128/328 |

FOREIGN PATENT DOCUMENTS

| | | | |
|---|---|---|---|
| 0168559 | 1/1986 | European Pat. Off. | |
| 3119295 | 12/1982 | Fed. Rep. of Germany | 128/328 |
| 3122056 | 12/1982 | Fed. Rep. of Germany | |
| 3220751 | 12/1983 | Fed. Rep. of Germany | 128/328 |
| 3417985 | 11/1985 | Fed. Rep. of Germany | |
| 8528785.7 | 7/1986 | Fed. Rep. of Germany | |
| 1421666 | 1/1976 | United Kingdom | |

Primary Examiner—Ruth S. Smith
Attorney, Agent, or Firm—Hill, Van Santen, Steadman & Simpson

[57] ABSTRACT

A lithotripsy work station for disintegrating a calculus in a patient has a patient support table on which the patient is disposed, a drive unit for selectively positioning the table, a shock wave generator, an x-ray system for generating a three dimensional visual representation of at least the region of the patient in which the calculus is disposed. The location of the focus of the shock wave generator is known with respect to the x-ray representation. A mark generator generates at least one mark superimposed on the x-ray representation, and also generates a signal which is supplied to the drive unit which causes the drive unit to position the table based on the position of the mark on the x-ray representation with respect to the position of the focus. A mark positioner is also provided for manually positioning the mark on the x-ray representation in coincidence with the calculus, so that the table is moved to a position with the patient thereon such that the focus coincides with the calculus for effective disintegration or shattering thereof.

4 Claims, 1 Drawing Sheet

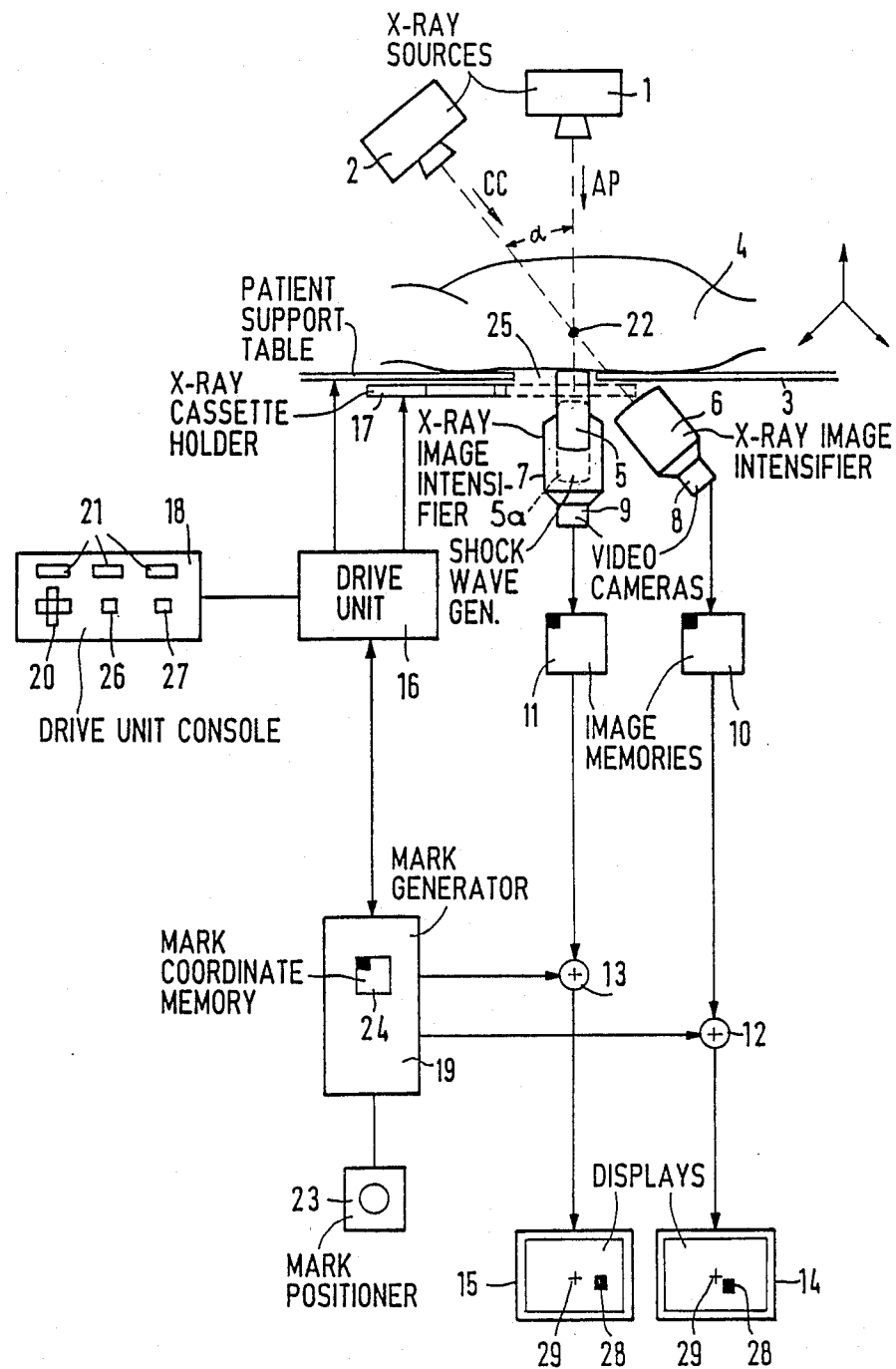

LITHOTRIPSY WORK STATION

BACKGROUND OF THE INVENTION

1. Field of the Invention

The present invention is directed to a lithotripsy work station, and in particular to such a work station having a three-dimensionally adjustable patient support table, a drive unit for moving the table, a shock wave generator for disintegrating calculi in a patient, and an x-ray examination means for locating the calculi within the patient and an image intensifier video chain for generating a visual image of the region of the patient in which the calculus is disposed.

2. Description of the Prior Art

A lithotripsy work station is disclosed in German Utility Model Registration No. 85 28 785 having two shock wave generators which can be swiveled from a standby position to an operating position. For locating the calculus to be disintegrated, the work station is equipped with an x-ray diagnostics system having two x-ray sources which generate respective intersecting x-ray beams. Each x-ray beam is converted into a visually displayable image by respective image intensifier video chains. The two x-ray beams intersect an an isocenter at which the shock wave generators are focussed when in the operating position.

When the calculus, for example a kidney stone or a gallstone, is recognized by the x-ray examination system, the calculus is brought to the isocenter, and thus to the focus of the shock wave generators, by displacing the patient support table. This is generally undertaken in the transillumination mode, thus exposing the patient to an undesireably high radiation dose.

SUMMARY OF THE INVENTION

It is an object of the present invention to provide a lithotripsy work station of the type described above which permits the patient support table to be displaced by means of stored x-ray exposures so as to bring the calculus to be treated into the focus of the shcok wave generator without unnecessarily exposing the patient to high radiation doses.

The above object is achieved in accordance with the principles of the present invention in a lithotripsy work station wherein a mark generator is provided for mixing a mark into each of the image intensifier vide chains. The mark corresponds to a spatial point above the patient support table, and a mark positioner is also provided so that the position of the mark on each of the video displays can be manually adjusted. The mark generator is also connected to the drive unit for the patient support table for providing a signal thereto so as to move the table to a working position wherein the spatial point is in the focus of the shock wave generator. The position of the focus of the shock wave generator with respect to each of the x-ray image displays is known, and the mark is manually positioned to be coincident with the image of the calculus on the x-ray image. The positon of the mark, and thus the position of the calculus, with respect to the known position of the focus is then known, and the patient support table is positioned accordingly.

Two x-ray images obtained in different planes can be stored at a beginning of the treatment, and a displaceable mark can be superimposed on the monitor for each image. Positioning of the mark, and thus positioning of the patient support table, can then be undertaken based on the stored images, without continually exposing the patient to radiation.

The working position which has been determined in this manner can then be again achieved at any subsequent time without further transillumination of the patient in an embodiment wherein the mark generator includes a memory for the coordinates of the working position. A high resolution x-ray exposure for documenting the intermediate status of the calculus, such as when an initial shock treatment is to be followed by subsequent shock treatments, can be moved in an embodiment of the work staion from a standby position to an exposure position under the patient support table. After the exposure has been made, the cassette holder can be moved back to the standby positon, and the patient support table can be automatically returned to the stored working position. The x-ray exposure cassette can thus be moved to its optimum exposure position without being disturbed by the shcok wave generator or the image intensifier, and after the exposure has been made, the patient support table can be returned to the working position for further treatment, if necessary.

DESCRIPTION OF THE DRAWINGS

The single FIGURE is a schematic block diagram of a lithotripsy work station constructed in accordance with the principles of the present invention.

DESCRIPTION OF THE PREFERRED EMBODIMENTS

The lithotripsy work station shown in the drawing includes an x-ray diagnostics system having two x-ray sources 1 and 2 which generate respective x-ray beams which penetrate a patient 4 situated on a patient support table 3. At least one shock wave generator 5 and two x-ray image intensifiers 6 and 7 are arranged beneath the patient support table 3. The x-ray source 1 and the x-ray image intensifier 7 may be arranged such that a central ray of the x-ray beam from the x-ray source 1 is perpendicularly incident on the patient 4 (a.p. projection). The x-ray source 2 and the x-ray image intensifier 6 may be arranged obliquely with respect to the first central ray such that the central ray from the x-ray source 2 intersects the central ray of the x-ray tube 1 at the isocenter inside the patient 4 at an angle $\alpha$ of, for example, 45° (c.c. projection). Transillumination images are thus obtained from two different projection directions, so that the patient can be three-dimensionally shifted by means of the patient support table 3 to position an object 22 within the patient, for example a kidney stone or a gallstone, at the isocenter, and thus in the focus of the shock wave generator 5.

An opening 25 is provided in the patient support table 3, and the shock wave generator 5 can be swiveled from a standby position 5a shown in dashed lines to the operating position shown in solid lines in the drawing through this opening. When in the operating position, the focus of the shock wave generator 5 is directed at the isocenter, so that shock wave treatment can be undertaken in the operating position, and the object 22 can be disintegrated.

Video cameras 8 and 9 are respectively coupled to the x-ray image intensifiers 6 and 7, the outputs of which are respectively entered in two image memories 10 and 11. Respective output signals from the image memories 10 and 11 are supplied to inputs of respective addition stages 12 and 13, the outputs of which are supplied to respective monitors 14 and 15 for visual reproduction of the x-ray images.

After transillumination of the patient, or at least a region thereof wherein the object 22 is situated, has been undertaken using the x-ray sources 1 and 2, the x-ray images are converted into video signals which are stored in the image memories 10 and 11.

The patient support table 3 is three-dimensionally positionable (as indicated by the three axes) by a drive unit 16 which controls the operation of respective motors (not shown). The drive unit 6 also controls positioning of an x-ray exposure means, for example, a cassette holder 17, also disposed beneath the patient support table 3. The cassette holder 17 can be moved from the standby position shown in solid lines in the drawing to an exposure position indicated by dashed lines by operation of the drive unit 16. The drive unit 16 had an operating console 18 for entering the required functions. For example, the patient support table 3 may be three-dimensionally displaced by actuating an adjustment control 20, and the current position of the patient support table 3 can be seen on the operating console 18 by display means 21 for the three spatial coordinates x, y and z.

A mark generator 19 is also connected to the drive unit 16, as well as to respective inputs of the addition stages 12 and 13. The mark generator 19 generates a mark 28 which is mixed into each of the video change so as to be superimposed on the x-ray images on the monitors 14 and 15. The mark 28 can be positioned on each of the displays by a mark positioner 23. For example, the mark 28 can be displaced on the image on the monitor 15 by the positioner 23 so that identification of the object 22 in the x-direction and y-direction (horizontal directions) is determined. Subsequently, the apparatus is switched so that the mark 28 on the monitor 14 can be positioned to be coincident with the image of the object 22, so that the position of the object in the z-direction (vertical direction) can be identified. When the marks 28 have been brought into coincidence with the image of the object 22 on each screen, the current coordinates of the marks 28 are stored in a memory 24 which may, for example, be contained within the mark generator 19. The position of the isocenter (illustrated by a graticule) with respect to each of the display images is known, so that the distance of the mark 28 from the isocenter can be calculated, and a signal corresponding to this distance can be generated and stored. By actuating a trigger knob 26 on the operating console 18, the patient support table 3 is then displaced by the drive unit 16 on the basis of a signal provided by the mark generator 19 so that the object 22 is situated at the isocenter, and thus at the focus of the shock wave generator 5. At the same time, the coordinates of this position of the patient support table 3 are entered in the memory 24 as the working position.

The mark positioner 23 may consist of a so-called track ball or "mouse." The mark positioner 23, however, may alternatively be a light cursor, respective potentiometers allocated to the three spatial coordinates, or a resistance film.

After shock wave treatment has been undertaken, an x-ray exposure can be made for intermediate supervision of the treatment, or for documenting the final patient status. The patient support table 3 can then be moved from the working position by actuating the trigger knob 27, so that the cassette holder 17 can be displaced from the illustrated standby position to the exposure position beneath the patient 4. The x-ray source 1 is then triggered to make the exposure. The cassette holder 17 is then returned to the standby position and the patient support table 3 is returned to the working position on the basis of the coordinates stored in the memory 24, so that the shock wave treatment can be continued as needed. The lithotripsy work station disclosed herein thus permits the radiation load on the patient to be maintained at a low level, because adjustment of the patient support table need not be undertaken while the patient is undergoing continuous transillumination.

Although modifications and changes may be suggested by those skilled in the art it is the intention of the inventors to embody within the patent warranted hereon all changes and modifications as reasonably and properly come within the scope of their contribution to the art.

We claim as our invention:

1. A lithotripsy work station for disintegrating a calculus in a patient comprising:
   a patient support table on which said patient is disposed;
   drive means for selectively positioning said patient support table;
   a shock wave generator having a focus;
   means for generating a three-dimensional visual x-ray representation of at least a region of said patient in which said calculus is disposed and wherein the position of said focus is known;
   means for generating at least one mark superimposed on said x-ray representation and for generating a signal for controlling said drive means to position said patient support table based on the position of said mark in said x-ray representation with respect to the position of said focus;
   means for manually positioning said mark on said x-ray representation in coincidence with the image of said calculus, thereby causing said means for generating said mark to control said drive means to position said patient support table at a work position at which said calculus is coincident with said focus; and
   a memory means for storing the coordinates of said work position so that said support table can be moved from and returned to said work position without further subjecting said patient to x-rays from said means for generating a three-dimensional visual x-ray representation.

2. A lithotripsy work station for disintegrating a calculus in a patient comprising:
   a patient support table on which said patient is disposed;
   drive means for selectively positioning said patient support table;
   a shock wave generator having a focus;
   means for generating a three-dimensional visual x-ray representation of at least a region of said patient in which said calculus is disposed and wherein the position of said focus is known;
   means for generating at least one mark superimposed on said x-ray representation and for generating a signal for controlling said drive means to position said patient support table based on the position of said mark in said x-ray representation with respect to the position of said focus;
   means for manually positioning said mark on said x-ray representation in coincidence with the image of said calculus, thereby causing said means for generating said mark to control said drive means to position said patient support table at a work position at which said calculus is coincident with said focus;

a memory for storing the coordinates of said work position;

an x-ray exposure apparatus connected to said drive means and moveable by said drive means from a standby position to an exposure position beneath said patient; and said drive means positioning said x-ray exposure apparatus in said exposure position and positioning said patient support table for making an x-ray exposure, and thereafter automatically returning said patient support table to said working position based on the coordinates stored in said memory.

3. A lithotripsy work station for disintegrating a calculus in a patient comprising:

a patient support table on which said patient is disposed;

drive means for selectively positioning said patient support table;

a first x-ray source disposed such that a central ray therefrom penetrates said calculus;

a second x-ray source disposed such that a central ray therefrom penetrates said calculus at an angle with respect to said central ray from said first x-ray source;

a shock wave generator having a focus;

means for generating a mark corresponding to a position above said patient support table;

a first video chain including a display on which the position of said focus is identified for generating and displaying a video image of x-rays from said first x-ray source attenuated by said patient;

a second video chain including a further display on which the position of said focus is identified for generating and displaying a video image of x-rays from said second x-ray source attenuated by said patient;

means for mixing said mark into each video chain such that said mark is superimposed on said display and said further display;

said mark generator also including means for generating a control signal for said drive means for positioning said patient support table based on the position of said mark on said display and on said further display with respect to said focus;

means for manually positioning said mark on said display and said further display coincident with said calculus, thereby causing said means for generating said mark to control said drive means to position said patient support table in a working position such that said focus is coincident with said calculus; and a memory means for storing the coordinates of said work position so that said support table can be moved from and returned to said work position without further subjecting said patient to x-rays from said first and second x-ray sources.

4. A lithotripsy work station for disintegrating a calculus in a patient comprising:

a patient support table on which said patient is disposed;

drive means for selectively positioning said patient support table;

a first x-ray source disposed such that a central ray therefrom penetrates said calculus;

a second x-ray source disposed such that a central ray therefrom penetrates said calculus at an angle with respect to said central ray from said first x-ray source;

a shock wave generator having a focus;

means for generating a mark corresponding to a position above said patient support table;

a first video chain including a display on which the position of said focus is identified for generating and displaying a video image of x-rays from said first x-ray source attenuated by said patient;

a second video chain including a further display on which the position of said focus is identified for generating and displaying a video image of x-rays from said second x-ray source attenuated by said patient;

means for mixing said mark into each video chain such that said mark is superimposed on said display and said further display;

said mark generator also including means for generating a control signal for said drive means for positioning said patient support table based on the position of said mark on said display and on said further display with respect to said focus;

means for manually positioning said mark on said display and said further display coincident with said calculus, thereby causing said means for generating said mark to control said drive means to position said patient support table in a working position such that said focus is coincident with said calculus;

a memory for storing the coordinates of said work position;

an x-ray exposure apparatus connected to said drive means and moveable by said drive means from a standby position to an exposure position beneath said patient; and said drive means positioning said x-ray exposure apparatus in said exposure position and positioning said patient support table for making an x-ray exposure, and thereafter automatically returning said patient support table to said working position based on the coordinates stored in said memory.

* * * * *